(12) United States Patent
Wolf (10) Patent No.: US 9,856,559 B2
(45) Date of Patent: Jan. 2, 2018

(54) CORONA TREATMENT SYSTEM

(71) Applicant: Illinois Tool Works Inc., Glenview, IL (US)

(72) Inventor: Rory A. Wolf, Hartford, WI (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 159 days.

(21) Appl. No.: 15/016,807

(22) Filed: Feb. 5, 2016

(65) Prior Publication Data

US 2017/0226632 A1 Aug. 10, 2017

(51) Int. Cl.
| | |
|---|---|
| G01J 3/46 | (2006.01) |
| C23C 16/02 | (2006.01) |
| G01J 3/50 | (2006.01) |
| G01N 21/952 | (2006.01) |

(52) U.S. Cl.
CPC .............. C23C 16/02 (2013.01); G01J 3/50 (2013.01); G01N 21/952 (2013.01)

(58) Field of Classification Search
CPC ...... G01J 3/02; G01J 3/50; G01J 3/46; G01N 21/952; C23C 16/02
See application file for complete search history.

(56) References Cited

U.S. PATENT DOCUMENTS

| | | | |
|---|---|---|---|
| 5,169,450 A | 12/1992 | Opad et al. | |
| 5,278,409 A | 1/1994 | Bonner | |
| 5,293,043 A | 3/1994 | Bonner | |
| 5,332,897 A | 7/1994 | Stobbe et al. | |
| 5,572,304 A * | 11/1996 | Seto | G03G 7/0006 399/313 |
| 6,007,784 A | 12/1999 | Jorgensen | |
| 6,894,279 B2 | 5/2005 | Washebeck et al. | |

FOREIGN PATENT DOCUMENTS

| | | |
|---|---|---|
| EP | 1187279 A2 | 3/2002 |
| EP | 2211434 A1 | 7/2010 |

OTHER PUBLICATIONS colorSENSOR OT-3-MA-30 Instruction Manual, Micro-Epsilon, 2008, 10 pages.
OT-3-MA-50-12.5, OT-3-MA-50-25, Fixed Lens Color Sensors for Special Targets, colorSENSOR OT-3-MA, Micro-Epsilon, 2 pages.
International Search Report and Written Opinion for International Patent Application No. PCT/US2016/067135 dated May 9, 2017, 13 pages.

* cited by examiner

*Primary Examiner* — Abdullahi Nur
(74) *Attorney, Agent, or Firm* — Klintworth & Rozenblat IP LLP (57) ABSTRACT

According to an aspect of the present disclosure, a color sensor is provided for sensing whether a ground roller in a corona treatment system needs to be serviced. The color sensor is capable of detecting imperfections which have changed the reflectance level of the ground roller from a predefined level. According to another aspect of the present disclosure, if a determination is made that the ground roller needs to be serviced, then an alarm is activated and/or the operation of the corona treatment system is ceased.

20 Claims, 7 Drawing Sheets

CORONA TREATMENT SYSTEM

FIELD OF THE INVENTION

The present invention relates generally to corona treatment of a web. More particularly, it relates to a color sensor capable of detecting imperfections on a ground roller used in a corona treatment system, to indicate that the ground roller needs to be serviced.

BACKGROUND

Corona treatment is a method using an electrical corona discharge to modify a surface of a web to improve its ability to accept inks and adhesives. In a corona treatment, a high voltage electrode is mounted parallel to and spaced from a ground roller, which forms a grounded electrode. The air gap between the electrodes is energized, forming a corona, which, when web is passed therethrough modifies the material the web is formed of, and makes the web more receptive to ink and adhesives. Corona will be produced anywhere there is air within this air gap.

The occurrence known as "backside treat" is the result of a corona being produced on both sides of a web being treated, even though the corona treatment system is only intended to treat one side of the web. The resulting undesired treatment on the backside of the web may result in blocking and picking. The resulting undesired treatment on the backside of the web may also cause an insufficient treat level on the side of the web requiring treatment, since some the power intended for treating the web was delivered to the opposite side, thus, reducing the watt density provided to the side to be treated.

There are a number of causes for backside treat, all of which are the result of air being entrapped under the web being treated. One of the most common causes for backside treat is dirt buildup on the corona ground roll. Regardless if the corona treatment system is a bare roll or a covered roll, dirt buildup gets deposited on the surface of the ground roller. These uneven deposits of dirt buildup lift the web off the surface of the ground roller, entrapping air underneath the web. To eliminate backside treat caused by dirt buildup, the ground roller must be cleaned.

SUMMARY

In one aspect, a color sensor capable of detecting whether a ground roller used in a corona treatment system needs to be serviced is provided. The color sensor is capable of detecting imperfections which have changed the reflectance level of the ground roller from a predefined level.

In another aspect, if a determination is made that the ground roller needs to be serviced, then an alarm is activated and/or the operation of the corona treatment system is ceased.

The scope of the present invention is defined solely by the appended claims and is not affected by the statements within this summary.

BRIEF DESCRIPTION OF THE DRAWINGS

The invention can be better understood with reference to the following drawings and description. The components in the figures are not necessarily to scale, emphasis instead being placed upon illustrating the principles of the invention.

DETAILED DESCRIPTION

While the invention may be susceptible to embodiment in different forms, there is shown in the drawings, and herein will be described in detail, specific embodiments with the understanding that the present disclosure is to be considered an exemplification of the principles of the invention, and is not intended to limit the invention to that as illustrated and described herein. Therefore, unless otherwise noted, features disclosed herein may be combined together to form additional combinations that were not otherwise shown for purposes of brevity.

The drawings illustrates a corona treatment system 20 which incorporates features of the present disclosure. The corona treatment system 20 may be adapted to be used in conjunction with a printing press (not shown). The corona treatment system 20 includes a cylindrical ground roller 22, a high voltage electrode 24, and a color sensor 26 for sensing imperfections on the surface 22a of the ground roller 22. Imperfections as defined herein are items on the ground roller 22 which change the reflectance level of the ground roller 22 from a predefined level. For example, imperfections can be caused by debris on the ground roller 22, water on the ground roller 22, oxidation on the ground roller 22, pitting on the ground roller 22. The corona treatment system 20 is used to modify a surface of a flexible web (not shown) to improve its ability to accept inks and adhesives. The web is passed between the ground roller 22 and the electrode 24 during which the material of web is treated to modify the material. Examples of webs that may be treated by the corona treatment system 20 include, but are not limited to, paper, polymer films, elastomers, plastics, foams, etc.

In general, the corona treatment system 20 includes a power supply cabinet 30 with a control panel 32 from which depends a first end plate 34 and, in parallel relationship thereto, a second end plate 36, the ground roller 22 rotatably mounted between the plates 34, 36, the color sensor 26 in proximity to the ground roller 22, an electrode support tube 38 mounted between the plates 34, 36, an electrode magazine 40 mounted on the electrode support tube 38 and supporting the high voltage electrode 24 in spaced relationship from the ground roller 22, a plurality of idler rollers 42 rotatably mounted between the plates 34, 36 and spaced from the ground roller 22, and an apparatus 400 provided within the cabinet 30 which communicates with the color sensor 26 and controls a display and/or light 46 on the cabinet 30. Tie bars 48 may be provided between the end plates 34, 36. The color sensor 26 is in proximity to the ground roller 22 so that the color sensor 26 can sense the reflectance levels of the ground roller 22. The color sensor 26 may be mounted on one of the end plates; as shown, the color sensor 26 is mounted on end plate 34; the color sensor 26 may be mounted on the ground.

The electrode support tube 38 and electrode magazine 40 mounted thereon may be pivotally connected to the end plates 34, 36 as is known in the art. Alternatively, the electrode magazine 40 may be slidably mounted on the electrode support tube 38 as is known in the art. This allows the electrode magazine 40 to be moved between an inoperative or maintenance position, and an operative or web treating position. The electrode support tube 38 is hollow and has an open end 50. The electrode support tube 38 has a plurality of apertures 52 therethrough which face the ground roller 22. Venting of ozone generated during the corona treatment and cooling for the electrode 24 is provided by the path formed by the apertures 52, the electrode support tube 38 and its open end 50 in a known manner.

The electrode magazine 40 has a pair of shields 54, 56 which are connected to the electrode support tube 38, and support tubes 58 for supporting the electrode 24 between the shields 54, 56. As such, the shields 54, 56 aid in guiding the ozone to be vented through the electrode support tube 38.

The electrode 24 may be a plurality of parallel electrodes; the electrode 24 may be a ceramic electrode, a FIN electrode, a segmented electrode, as is known in the art.

Figure 1:
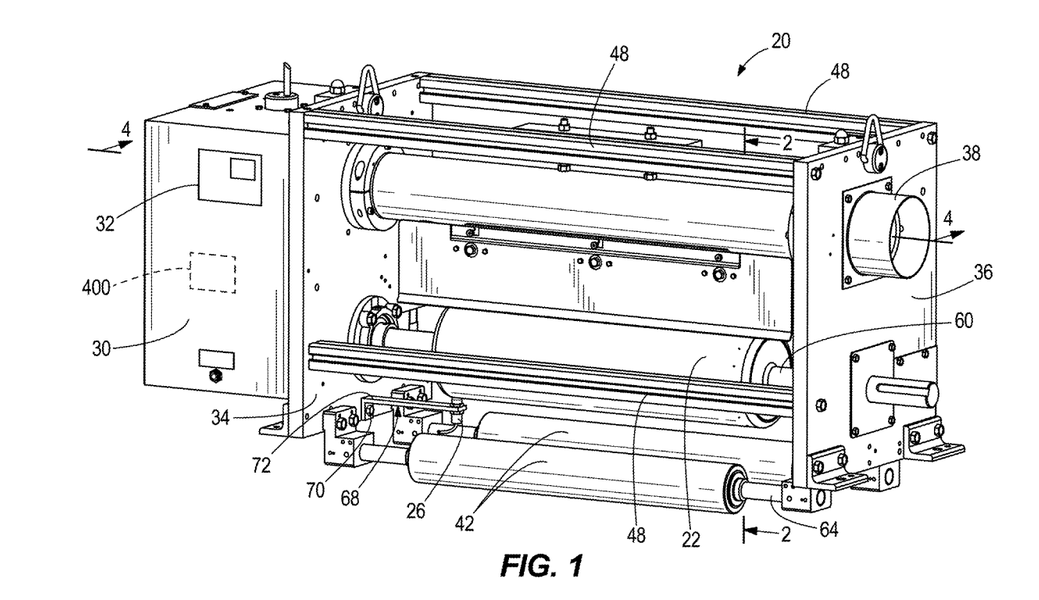
FIG. 1 depicts a perspective view of a corona treatment system which incorporates features of the present disclosure.
Figure 2:
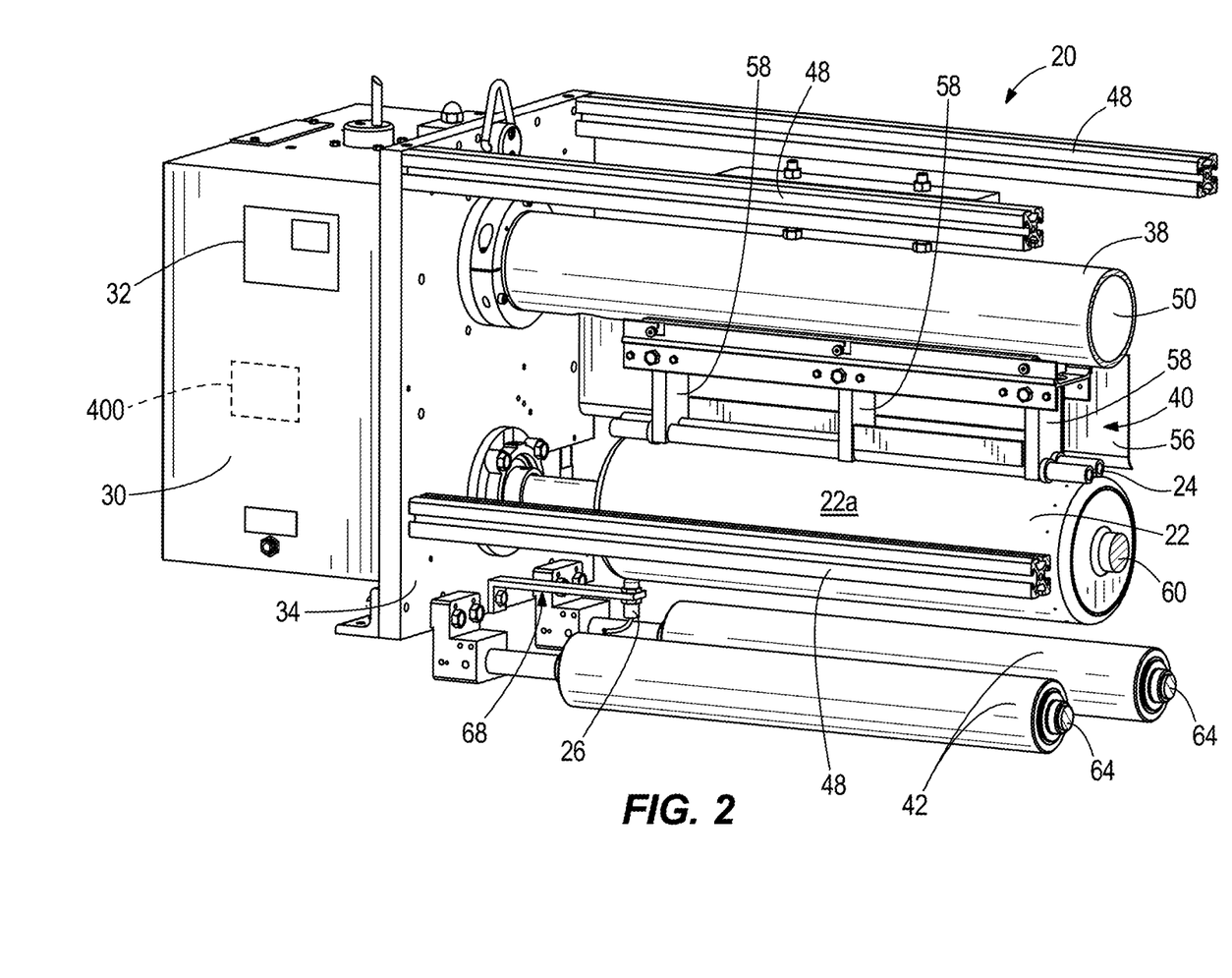
FIG. 2 depicts an alternate perspective view of a portion of the corona treatment system, with curtains removed to show features of the present system.
Figure 3:
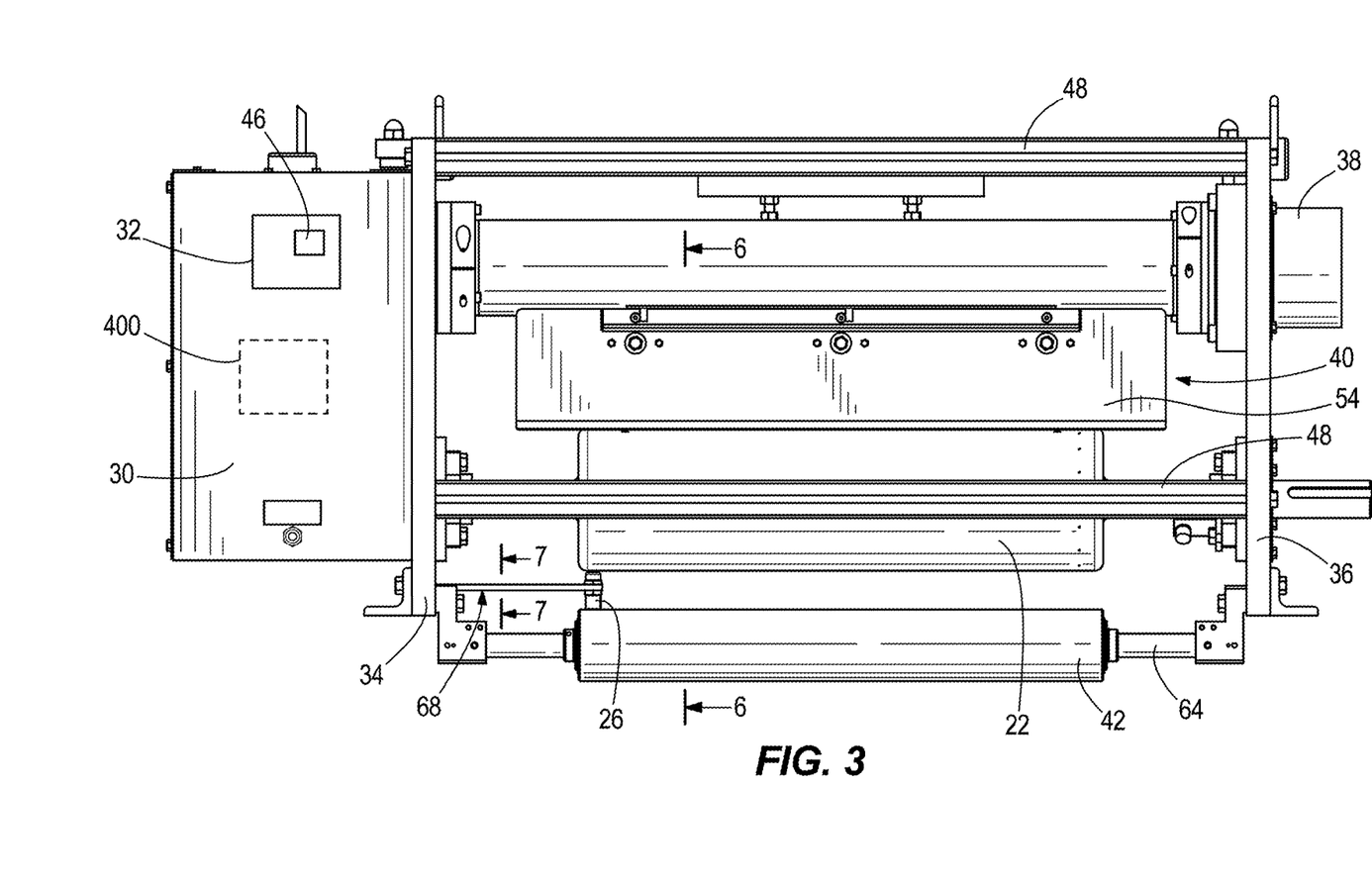
FIG. 3 depicts a side elevation view of the corona treatment system.
Figure 4:
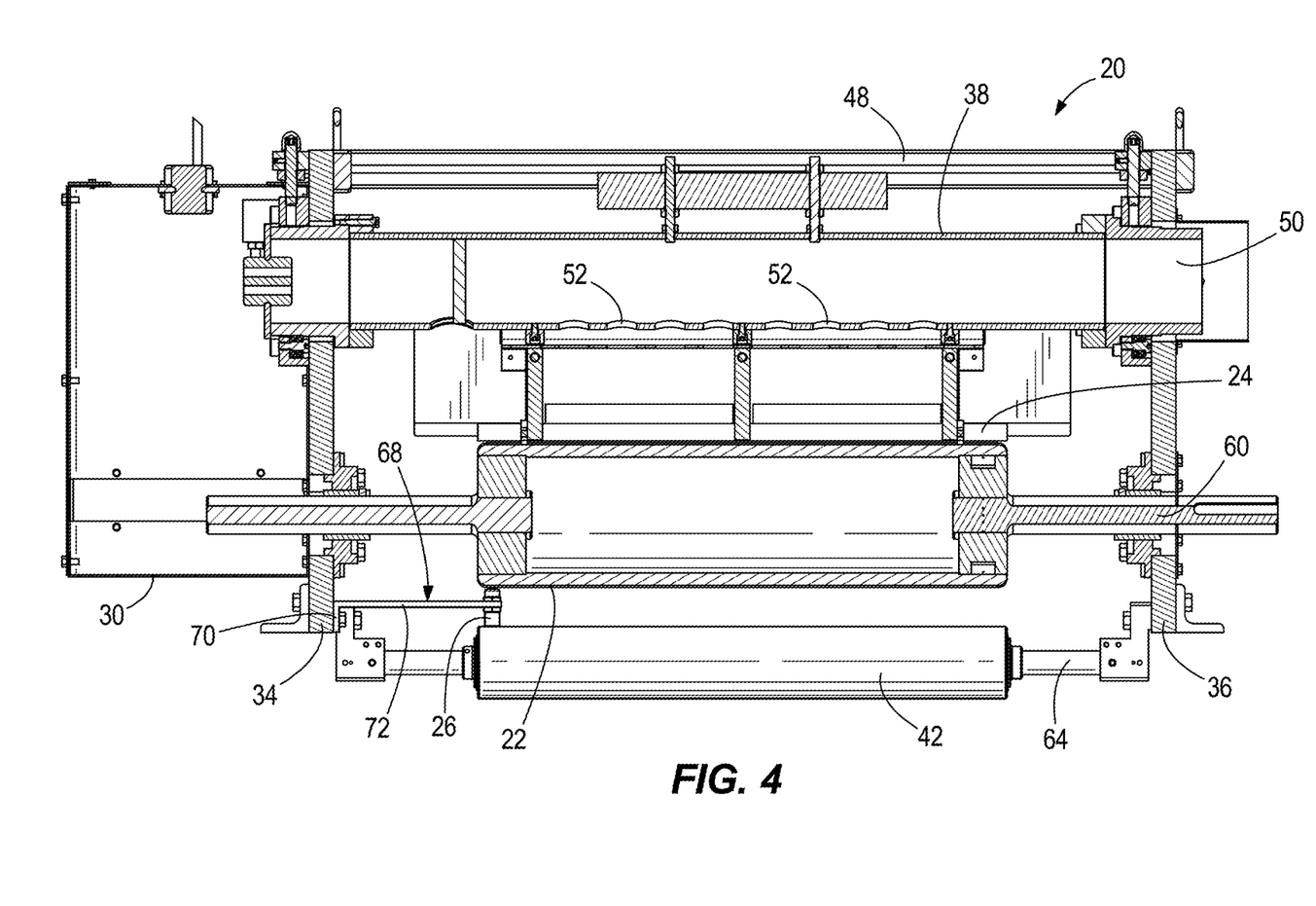
FIG. 4 depicts a cross-sectional view of the corona treatment system along line 4-4 of FIG. 1.
Figure 5:
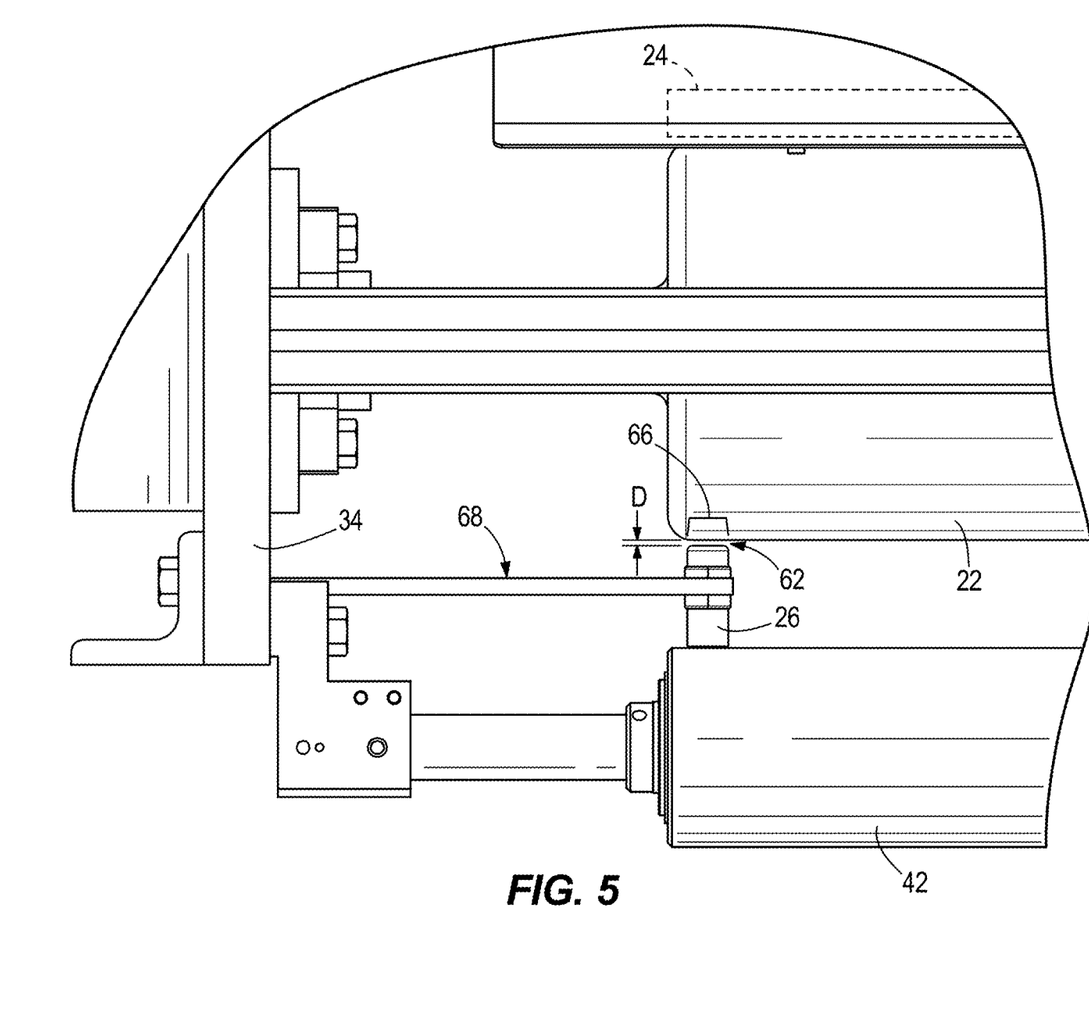
FIG. 5 depicts an enlarged partial view of the corona treatment system.

The ground roller 22 is mounted for a rotation on a shaft 60 between the end plates 34, 36 and is positioned beneath the support tube 22 and beneath the electrode 24. The electrode 24 may span the length of the ground roller 22. The ground roller 22 and the electrode 24 may be spaced 1.5 mm away from each other to form an air gap 62, see FIGS. 5 and 6. Ground rollers used in corona treatment systems are known in the art. The ground roller 22 may have a surface 22a formed of steel, ceramic, rubber, etc. The ground roller 22 may be formed of a self-supporting tube of a rigid dielectric material, such as a glass fiber reinforced epoxy or a glass fiber reinforced polymeric polyester. A conductive layer may be bonded to an inner wall of the ground roller 22. The conductive layer is a relatively thin conductive metallic film or a coating containing a conductor, such as graphite. The conductive layer is relatively thin and does not have to be self-supporting because it is supported by the inner wall of the roller.

The idler rollers 42 are mounted for rotation on respective shafts 64 between the end plates 34, 36, and lie in space relationship below the ground roller 22.

The power supply cabinet 30 includes a power supply and a high voltage transformer provided with a high voltage wire. The wire terminates in a high voltage connection normally enclosed by a high voltage cover plate located behind the end plate 34. The high voltage connection establishes a high voltage field between the ground roller 22 and the electrode 24 with the web to be treated interposed between the electrode 24 and the ground roller 22. As is well known, the high voltage field establishes a corona discharge that causes the chemical composition of the material of the web to be modified which, in turn, improves selected characteristics of the material of the web such as wettability so that printed matter or coating may be more advantageously adhered thereto.

In use, the web is guided upwardly by the idler rollers 42 and wound about the ground roller 22 in spaced relationship from the electrode 24. The web does not span the entire length of the ground roller 22 such that there is a portion 66 exposed at least one end of the ground roller 22. The electrode 24 spans this portion 66 such that the surface 22a of this portion 66 of the ground roller 22 is subjected to the high voltage from the electrode 24. The ground roller 22 supports the web which is treated as it passes through the air gap 62 between the ground roller 22 and the electrode 24 in a direction transverse to the longitudinal direction of the electrode 24. The air gap 62 between the two electrodes 22, 24 is normally about 1.5 mm wide and a corona discharge develops in the air gap 62 when the electrode 24 is energized by the power supply to create a high voltage. The surface of the web passing through the air gap 62 is modified by the exposure to the corona so that its printing properties are improved. However, the high frequency voltage generated by the electrode 24 is also applied to the ground roller 22. This causes the ground roller 22 to be heated which causes imperfections, such as oxidation and pitting, on the surface 22a of the ground roller 22. These imperfections will be present on the portion 66 of the ground roller 22 and are detected by the color sensor 24.

Figure 6:
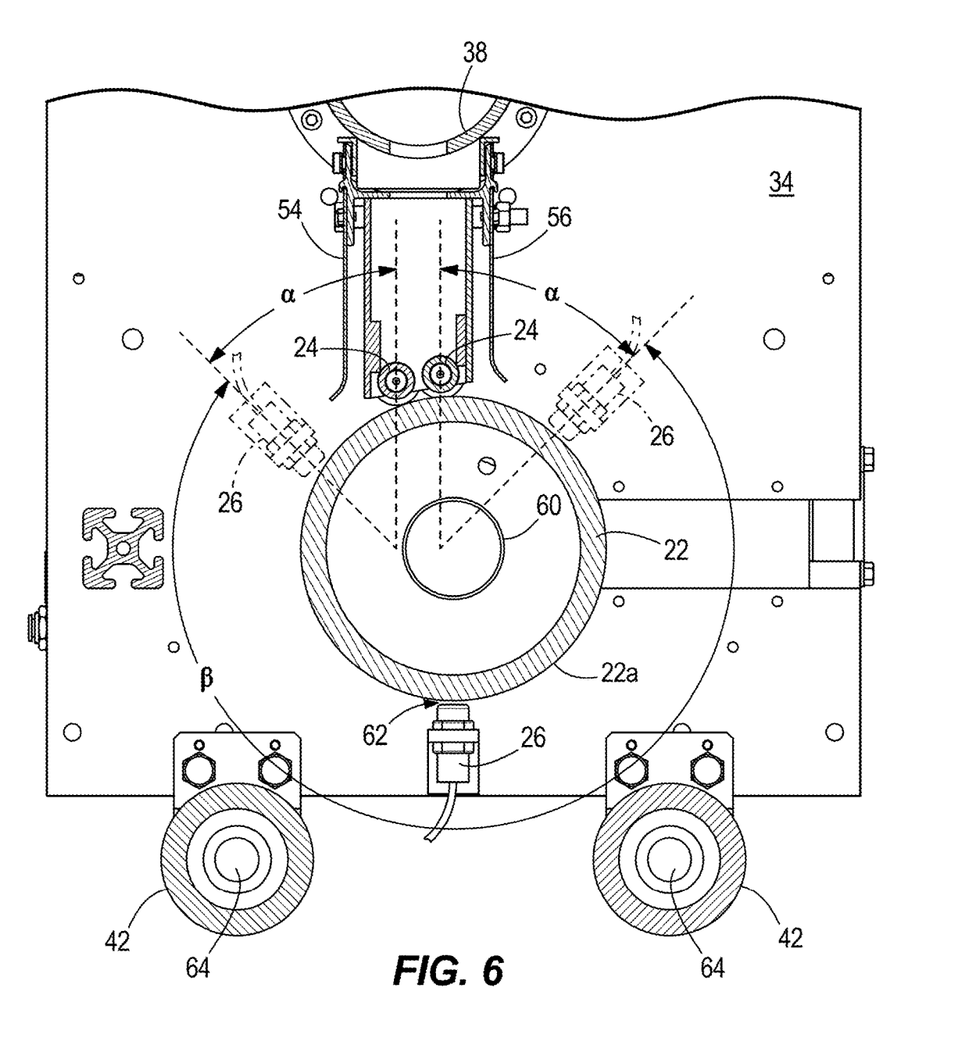
FIG. 6 depicts a cross-sectional view of the corona treatment system along line 6-6 of FIG. 3.

The color sensor 26 has a specific reflectance monitoring capacity and is mounted at a defined distance D from the ground roller 22. The color sensor 26 is resistant to dust, water, debris, heat and ozone; such a sensor is commonly designated as a IP64 sensor. The color sensor 26 may be mounted in a variety of positions relative to the circumference of the ground roller 22 as shown in FIG. 6. As shown in FIG. 6, the color sensor 26 (shown in full line) may mounted so as to be generally diametrically opposed to the electrode 24. The color sensor 26 is spaced a minimum at an angle α which is 45 degrees away from the electrode 24 as shown in FIG. 6. A variety of mounting positions for the color sensor 26 are shown in FIG. 6, but the sensor 26 can be mounted at any position around the circumference of the ground roller 22 through the arc shown by arrow β.

The color sensor 26 illuminates the portion 66 of the surface of the ground roller 22 with white light and captures and analyzes the reflected color values. The color sensor 26 is pre-programmed to recognize a base reflectance state at the ground roller 22 which represents a "clean" appearance of the ground roller 22, that is a state where there are no imperfections on the ground roller 22. The color sensor 26 is pre-programmed to recognize an "unacceptable reflectance state" at the ground roller 22 representing a threshold contaminated appearance of the ground roller 22, that is, when there are imperfections on the ground roller 22. Since the imperfections will be present on the portion 66 of the ground roller 22, once the portion 66 of the ground roller 22 proximate to the color sensor 26 reaches the unacceptable reflectance state, a signal is sent from the color sensor 26 to the apparatus 400 to activate an alarm 401 and/or to cease operation of the corona treatment system 20. An example of a suitable color sensor 26 is sold under the tradename colorSENSOR 26 OT-3-MA sold by MICRO-EPSILON MESSTECHNIK GmbH & Co. KG.

The color sensor 26 is positioned such that the color sensor 26 directs its light beam onto the portion 66 of the ground roller 22 that is not covered by the web during the corona treatment of the web. As shown, the color sensor 26 is positioned proximate to an end of the ground roller 22.

The color sensor 26 may be mounted on an arm 68 extending from the end plate 34. The arm 68 of the color sensor 26 is moveable relative to the end plate 34 so that the color sensor 26 can be moved toward or away from the ground roller 22 a predetermined distance, for example, the color sensor 26 may be positioned 2 to 5 inches away from the ground roller 22 to provide a sensing diameter of 0.5 inches to 2 inches on the ground roller 22; the sensing diameter is dependent upon the diameter of the ground roller 22. The arm 68 can be moved, thus moving the color sensor 26, and then fixed into a new position relative to the end plate 34. The color sensor 26 may be moved to accommodate differently sized ground rollers and to minimize any shadowing.

Figure 7:
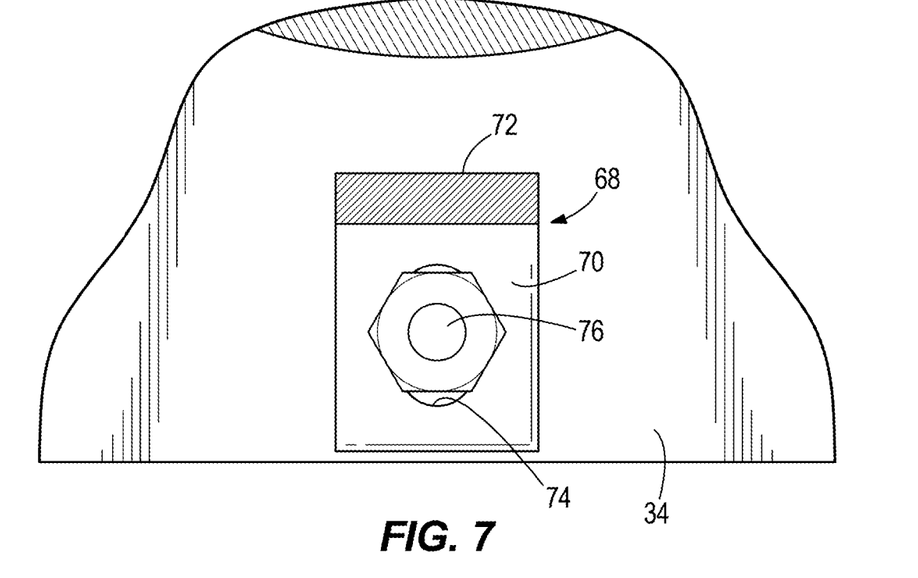
FIG. 7 depicts a cross-sectional view of the corona treatment system along line 7-7 of FIG. 3.

As shown, the arm 68 has a first portion 70 which abuts against the end plate 34, and a second portion 72 which is perpendicular to the first portion 70. As shown in FIG. 7, the first portion 70 has a slot 74 through which a fastener 76 is seated. The fastener 76 is threaded into an aperture in the end plate 34. The color sensor 26 is attached to the free end of the second arm 68. To change the position of the color sensor 26 relative to the ground roller 22, the fastener 76 is loosened so that the arm 68 can be moved relative to the end plate 34. This allows the fastener 76 to translate within the slot 74, thereby allowing the arm 68 and color sensor 26 to move to a new position. Once the color sensor 26 is positioned in a desired new position, the fastener 76 is secured to prevent further relative movement between the arm 68/color sensor 26 and the end plate 34. The slot 74 could instead be provided on the end plate 34, with the aperture in the arm 68. It is to be understood that this structure for allowing relative movement between the color sensor 26 and end plate 34 is illustrative only and that many structures may be provided for allowing the relative movement between the color sensor 26 and end plate 34 which would be known to one of ordinary skill in the art.

As discussed, the color sensor 26 is used to sense a specific level of reflectance at the ground roller 22 and this information is supplied to the apparatus 400 which alerts an operator by an alarm 401, and/or is used by the apparatus 400 to cease the operation of the corona treatment system 20. The alarm 401 may take the form of an audible signal, a light, a combination of an audible signal and light, etc. The triggering of the alarm 401 may also be used by the apparatus 400 to cease operation of the corona treatment system 20. Once the operator is notified, the operator will then know that the ground roller 22 needs to be serviced.

Other sensors, such as a sensor (not shown) that detects air flow and a sensor (not shown) that detects the speed of the ground roller 22, may be provided in the corona treatment system 20.

Figure 8:
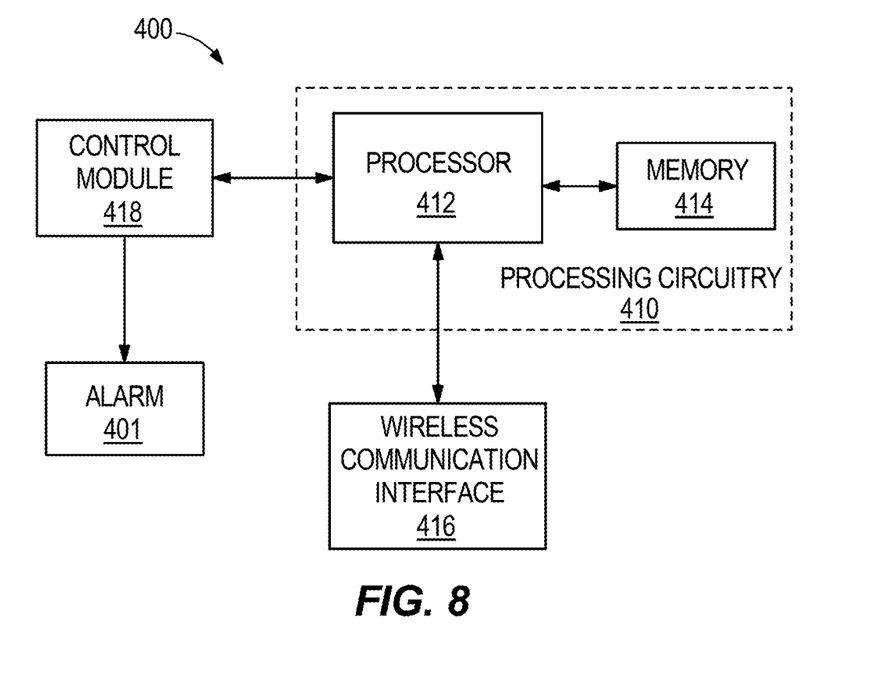
FIG. 8 depicts a block view of a control system.

FIG. 8 illustrates a block diagram of an apparatus 400 that may be implemented on the corona treatment system 20, in accordance with some example embodiments. In this regard, when implemented on a corona treatment system 20, apparatus 400 may enable the corona treatment system 20 to analyze information from the color sensor 26 to activate the alarm 401 and/or cease operation of the corona treatment system 20 in accordance with one or more example embodiments. It will be appreciated that the components, devices or elements illustrated in and described with respect to FIG. 8 below may not be mandatory and thus some may be omitted in certain embodiments. Additionally, some embodiments may include further or different components, devices or elements beyond those illustrated in and described with respect to FIG. 8.

In some example embodiments, the apparatus 400 may include processing circuitry 410 that is configurable to perform actions in accordance with one or more example embodiments disclosed herein. In this regard, the processing circuitry 410 may be configured to perform and/or control performance of one or more functionalities of the corona treatment system 20, such as actuating the roller 22 and the electrode 24, activating the color sensor 26 and analyzing the information from the color sensor 26 to activate the alarm 401 and/or cease operation of the corona treatment system 20 in accordance with various example embodiments. The processing circuitry 410 may be configured to perform data processing, application execution and/or other processing and management services according to one or more example embodiments.

In some embodiments, the apparatus 400 or a portion(s) or component(s) thereof, such as the processing circuitry 410, may include one or more chipsets and/or other components that may be provided by integrated circuits.

In some example embodiments, the processing circuitry 410 may include a processor 412 and, in some embodiments, such as that illustrated in FIG. 8, may further include memory 414. The processing circuitry 410 may be in communication with or otherwise control a wireless communication interface 416 in communication with the color sensor 26 (the color sensor 26 may be hard wired to the processing circuitry 410 and/or control module 418.

The processor 412 may be embodied in a variety of forms. For example, the processor 412 may be embodied as various hardware-based processing means such as a microprocessor, a coprocessor, a controller or various other computing or processing devices including integrated circuits such as, for example, an ASIC (application specific integrated circuit), an FPGA (field programmable gate array), some combination thereof, or the like. Although illustrated as a single processor, it will be appreciated that the processor 412 may comprise a plurality of processors. The plurality of processors may be in operative communication with each other and may be collectively configured to perform one or more functionalities of the apparatus 400 as described herein. In some example embodiments, the processor 412 may be configured to execute instructions that may be stored in the memory 414 or that may be otherwise accessible to the processor 412. As such, whether configured by hardware or by a combination of hardware and software, the processor 412 capable of performing operations according to various embodiments while configured accordingly.

In some example embodiments, the memory 414 may include one or more memory devices. Memory 414 may include fixed and/or removable memory devices. In some embodiments, the memory 414 may provide a non-transitory computer-readable storage medium that may store computer program instructions that may be executed by the processor 412. In this regard, the memory 414 may be configured to store information, data, applications, instructions and/or the like for enabling the apparatus 400 to carry out various functions in accordance with one or more example embodiments. In some embodiments, the memory 414 may be in communication with one or more of the processor 412 and transmission power control module 418 via one or more buses for passing information among components of the apparatus 400.

The apparatus 400 may further include circuitry, hardware, a computer program product comprising a computer readable medium (for example, the memory 414) storing computer readable program instructions that are executable by a processing device (for example, the processor 412), or some combination thereof. In some embodiments, the processor 412 (or the processing circuitry 410) may include, or otherwise control the transmission power control module 418.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

While various embodiments of the invention have been described, it will be apparent to those of ordinary skill in the art that other embodiments and implementations are possible within the scope of the invention. Accordingly, the invention is not to be restricted except in light of the attached claims and their equivalents.

The invention claimed is:

1. A corona treatment system comprising:
an end plate;
a rotatable ground roller mounted to the end plate;
a high-voltage electrode mounted to the end plate and mounted proximate to the ground roller; and
a color sensor in proximity to the ground roller, the color sensor capable of detecting imperfections on the ground roller.

2. The corona treatment system of claim 1, wherein the color sensor is mounted to the end plate.

3. The corona treatment system of claim 1, further comprising a second end plate to which the ground roller is attached.

4. The corona treatment system of claim 2, further comprising an arm to which the color sensor is mounted, the arm being connected to the end plate.

5. The corona treatment system of claim 2, wherein the arm is movably mounted to the end plate such that the position of the color sensor relative to the ground roller can be changed.

6. The corona treatment system of claim 1, wherein the color sensor is movable relative to the ground roller such that the position of the color sensor relative to the ground roller can be changed.

7. The corona treatment system of claim 1, wherein the color sensor generally diametrically opposed to the electrode.

8. The corona treatment system of claim 1, wherein the color sensor is positioned at an angle of 45 degrees or greater away from the electrode.

9. The corona treatment system of claim 1, further comprising a controller in communication with the color sensor, and an alarm in communication with the controller, wherein upon determination by the color sensor that the ground roller has imperfections, a signal is sent to the controller which activates the alarm.

10. The corona treatment system of claim 9, wherein the alarm is a light.

11. The corona treatment system of claim 9, wherein the alarm is an audible signal.

12. The corona treatment system of claim 1, further comprising a controller in communication with the color sensor, wherein upon determination by the color sensor that the ground roller has imperfections, a signal is sent to the controller which terminates operation of the electrode.

13. The corona treatment system of claim 1, wherein the color sensor is positioned proximate to an end of the ground roller.

14. A corona treatment system comprising:
an end plate;
a rotatable ground roller mounted to the end plate;
a high-voltage electrode mounted to the end plate and mounted proximate to the ground roller; and
a color sensor mounted to the end plate, the color sensor mounted such that a light beam of the color sensor is directed onto the ground roller proximate to an end of the ground roller, the color sensor capable of detecting imperfections on the ground roller, the color sensor being movable relative to the ground roller such that the position of the color sensor relative to the ground roller can be changed;
a controller in communication with the color sensor; and
an alarm in communication with the controller, wherein upon determination by the color sensor that the ground roller has imperfections, a signal is sent to the controller which activates the alarm.

15. A method of operating a corona treatment system comprising:
activating a high-voltage electrode in proximity to a ground roller to form a corona;
rotating the ground roller to move a web past the high-voltage electrode; and
sensing imperfections on the ground roller.

16. The method of claim 15, wherein a color sensor is used to send the imperfections on the ground roller.

17. The method of claim 15, further comprising activating an alarm if the sensed imperfections exceed a predetermined level.

18. The method of claim 15, further comprising ceasing operation of the electrode and ground roller if the sensed imperfections exceed a predetermined level.

19. The method of claim 15, further comprising activating an audible signal if the sensed imperfections exceed a predetermined level.

20. The method of claim 15, further comprising activating a visual signal if the sensed imperfections exceed a predetermined level.

* * * * *